United States Patent [19]

Devic et al.

[11] Patent Number: 4,717,451
[45] Date of Patent: Jan. 5, 1988

[54] PROCESS FOR THE PREPARATION OF ANTHRAQUINONE DISPERSIONS AND THEIR USE IN ALKALINE WOOD DIGESTION PROCESSES

[75] Inventors: Michel Devic, Sainte Foy les Lyon; Jean-Pierre Schirmann, Oullins, both of France

[73] Assignee: Atochem, France

[21] Appl. No.: 810,405

[22] Filed: Dec. 18, 1985

[30] Foreign Application Priority Data

Dec. 21, 1984 [FR] France ................................ 8420090

[51] Int. Cl.$^4$ .......................... C07C 50/18; D21C 3/20
[52] U.S. Cl. ..................... 162/72; 260/369; 162/76
[58] Field of Search ........................... 260/369; 162/72

[56] References Cited

U.S. PATENT DOCUMENTS

| | | | |
|---|---|---|---|
| 1,591,712 | 4/1926 | Lewis | 260/369 |
| 3,089,879 | 3/1963 | Serres, Jr. et al. | 260/369 |
| 4,002,653 | 3/1977 | Reuter et al. | 260/369 |
| 4,012,280 | 3/1977 | Holton | 162/72 |
| 4,045,456 | 8/1977 | Merger et al. | 260/369 |

FOREIGN PATENT DOCUMENTS

| | | | |
|---|---|---|---|
| 121466 | 10/1984 | European Pat. Off. | 260/369 |
| 583120 | 12/1977 | U.S.S.R. | 260/369 |

Primary Examiner—Glennon H. Hollrah
Assistant Examiner—Raymond Covington
Attorney, Agent, or Firm—Sigalos & Levine

[57] ABSTRACT

The process of making a wet or dry dispersion containing anthraquinone suitable for use in the alkaline digestion of wood comprising cyclizing ortho-benzoylbenzoic acid at a temperature of about 150° to 180° C. and at an absolute pressure between about 5 and 40 millibars in the presence of between about 0.05 to 2 parts by weight of sulfuric acid, having a concentration of at least about 95%, per part by weight of ortho-benzoylbenzoic acid to form a reaction mixture containing anthraquinone, bringing the reaction mixture to a pH of at least about 7 by addition thereto at a temperature between about ambient temperature and 100° C. of an aqueous solution of sodium hydroxide or potassium hydroxide containing between about 10% to 40% hydroxide by weight, and then forming a dispersion thereof and using such dispersion in the alkaline digestion of wood.

5 Claims, No Drawings

PROCESS FOR THE PREPARATION OF ANTHRAQUINONE DISPERSIONS AND THEIR USE IN ALKALINE WOOD DIGESTION PROCESSES

BACKGROUND OF THE INVENTION

This invention concerns a process for the preparation of anthraquinone.

More specifically, it concerns a modified process for producing anthraquinone by cyclization of ortho-benzoylbenzoic acid in the presence of sulfuric acid.

In addition to its application in the area of dyestuffs, anthraquinone is used in greater amounts and more widely in industry, particularly in the papermaking industry, to improve the alkaline digestion of wood, as described for example in the French Patent published under No. 2,373,637.

The delignification catalyst role which anthraquinone plays in this context is currently obtained when this product is employed in a highly purified form, which must therefore be achieved first.

Unfortunately, this sort of anthraquinone preparation represents an obvious economic burden in an industry such as the papermaking industry which produces an end-product of low market value.

The technical problem which the applicant attempted to solve was to obtain a process producing anthraquinone economically and in a form in which it could be used in an industry such as the papermaking industry to guarantee economic gain without loss of efficiency.

Cyclization of ortho-benzoylbenzoic acid, hereinafter referred to as OBB acid, by heating in the presence of a large quantity of concentrated sulfuric acid or oleum (cf., for example, I. Vogel, "Practical Organic Chemistry", 3rd edition, p. 740), isolating the resulting anthraquinone and purifying it, for example, by causing it to precipitate by diluting the reaction mixture with a large volume of water, isolating the precipitated anthraquinone by filtration and then washing it thoroughly with water to neutral pH to eliminate as many as possible of the residual impurities before drying, is a known process. Anthraquinone purified in this manner is generally prepared before use in the papermaking industry in the form of a dispersion in a solid inert product containing 50% anthraquinone by weight and produced by finely grinding the two constituents in the presence of a dispersing agent.

The methods of cyclizing OBB acid to produce purified anthraquinone such as is currently used in industry entail not only a high direct cost for this product, but also an additional consequential cost for decontamination of acid effluents before disposal. This initial high cost for anthraquinone is obviously inconsistent with its application in an industry such as the papermaking industry, which requires low-cost raw materials.

Attempts have been made to make the production of anthraquinone from OBB acid more economical. These have involved, for example, either reducing the quantity of sulfuric acid as described in Japanese Patent Application No. 49-7260/74 or the U.S. Pat. No. 2,842,562, or replacing the sulfuric acid with another catalyst such as clay as proposed in French Utility Patent No. 76.18056, Japanese Patent No. 49-6240/74 or the French Patent Application published under number 2,545,483.

In all of the above cases, since the processes are designed to produce purified anthraquinone, the advantages obtained in terms of the lowest possible materials cost are economically cancelled out by the higher cost engendered by the greater complexity of the equipment required.

SUMMARY OF THE INVENTION

The process according to the invention produces anthraquinone in a form which can be used both economically and efficiently in the papermaking industry.

Briefly stated, the present invention comprises the process of making a wet or dry dispersion containing anthraquinone suitable for use in the alkaline digestion of wood comprising cyclizing ortho-benzoylbenzoic acid at a temperature of about 150° to 180° C. and at an absolute pressure between about 5 and 40 millibars in the presence of between about 0.5 to 2 parts by weight of sulfuric acid, having a concentration of at least about 95%, per part by weight of ortho-benzoylbenzoic acid to form a reaction mixture containing anthraquinone, bringing the reaction mixture to a pH of at least 7 by addition thereto at a temperature between about ambient temperature and 100° C. of an aqueous solution of sodium hydroxide or potassium hydroxide containing between about 10% to 40% hydroxide by weight, and then forming a dispersion thereof.

The invention also comprises the process of using said dispersions in the digestion of wood as hereinafter described.

DETAILED DESCRIPTION

Within the range of values presented above, which are particularly suitable for the implementation of the process according to the invention, the optimum values are the following:

(a) during cyclization of the OBB acid:
  (i) relative quantity of sulfuric acid and OBB acid: between 0.6 and 1 part of $H_2SO_4$ by weight per part of OBB acid.
  (ii) temperature and absolute pressure: approximately 160° C., 10 millibars.

(b) during addition of the alkali metal hydroxide:
  (i) temperature and pressure: between 50° and 60° C., preferred pressure equal to atmospheric pressure for reasons of convenient processing, but can be less than or greater than this value.
  (ii) concentration of hydroxide solution: 20-30% by weight.

Under the general implementation conditions for the process, the duration of the operation is generally between 30 minutes and three hours. Under the preferred conditions presented, this duration is on the order of one hour.

The dispersion of the anthraquinone within the suspension resulting from addition of the hydroxide solution can be created by any known effective method as, for example, by means of a rotating disc grinder with sand, preferably in the presence of a dispersing agent such as, for example, sodium lignosulfonate.

The resulting dispersion can be used as is in the papermaking industry.

The dry dispersion of anthraquinone can be produced from the above-mentioned wet dispersion by drying the latter using any suitable known method as, for example, by atomization in a stream of hot air, after addition of additives conventionally used in similar cases, such as any known anti-clotting agent and anti-dusting agent.

For most effective use in the alkaline digestion of woods it is preferred that the dispersion contain at least about 20% by weight of anthraquinone.

The process according to the invention is particularly economical because, in particular, it does not involve the steps of filtration, washing and treatment of effluents contaminated with acid and/or organic substances.

It would normally be expected, however, that the presence of impurities such as, among others, unconverted OBB acid, phthalic acid and polycondensed products, alongside the anthraquinone, would greatly interfere with the specific catalytic activity of this product during delignification of the wood.

The examples given below are for purposes of illustration only and not to be considered limiting. They show that the catalytic activity during delignification is not interfered with and that the present invention advantageously and unexpectedly reconciles economics with efficiency.

EXAMPLE 1

Preparation of the anthraquinone dispersion according to the invention

In a glass rotary evaporator, 22.6 g of pure OBB acid marketed by the Merck Company and 22.6 g of 96% $H_2SO_4$ by weight are heated for one hour at 160° C. and an absolute pressure of 10 millibars.

Once this operation is finished, the mixture is brought to atomspheric pressure, and while the temperature is maintained at 80° C., its pH is brought to 9 by adding with agitation a solution of sodium hydroxide containing 30% NaOH by weight.

The resulting suspension is ground in a mortar to form a dispersion whose anthraquinone concentration is adjusted to 20% by weight by adding water.

Application of the dispersion for delignification of wood

Chips of resin-bearing pine are treated in an alkaline digestion bath in which the alkali content (sodium hydroxide) is 23% and the weight ratio between liquor and vegetative matter is 4 according to the following protocol: time to reach temperature of 170° C.=1.5 hours; time at temperature of 170° C.=1.5 hours.

The kappa index (French standard AFNOR N.F. T 12 018) of the final resulting paper pulp is determined for a test conducted under the conditions above (test 1) and under the same conditions but in the presence of a variable quantity of either purified anthraquinone at a concentration of 99% as supplied by the Bayer Company AG (test 2) or anthraquinone in the 20% dispersion in Example 1 (test 3).

The quantity of anthraquinone used each time is expressed as a weight percentage of the weight of dry wood.

Table 1 summarizes the results expressed as the kappa indices for the resulting pulps, which express the efficiency of delignification.

TABLE I

| Test | Anthraquinone, % | Kappa Index |
|---|---|---|
| 1 | 0 | 78.5 |
| 2 | 0.05 | 46.8 |
|  | 0.20 | 31.0 |
|  | 0.80 | 22.0 |
| 3 | 0.05 | 45.6 |
|  | 0.20 | 32.3 |

TABLE I-continued

| Test | Anthraquinone, % | Kappa Index |
|---|---|---|
|  | 0.80 | 29.8 |

EXAMPLE 2

After proceeding as in Example 1, but adding the sodium hydroxide solution at a temperature of 50° C. to bring the pH of the reaction mixture to 9, drying the dispersion obtained after the mortar-grinding stage in an oven at 110° C. and re-grinding after drying, the final result is 50.8 g of a powder containing 40% anthraquinone by weight.

This powder is utilized in place of the dispersion in Example 1 in a test otherwise entirely identical to test 3 in Table 1.

At anthraquinone concentrations of 0.05%, 0.20% and 0.80%, the following kappa indices were obtained: 46.3, 33.4 and 22.8, respectively.

EXAMPLE 3

After proceeding as in Example 2 with 22.6 g of Merck quality OBB acid and 14.95 g of sulfuric acid at 96% by weight, an absolute pressure of 6 millibars during the one-hour cyclization period at 160° C. and with addition of sodium hydroxide so that the pH of the mixture before grinding is 9, the final result is 41 g of a powder containing 50% anthraquinone by weight in the dispersed state.

When employed in alkaline wood-digestion tests such as those already described under the designation of Test 3, the anthraquinone contained herein was seen to have an efficiency similar in practically all ways to that of purfied anthraquinone.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. In the process of alkaline digestion of wood in a conventional alkaline wood-digestion bath, the improvement comprising adding to said digestion bath a dispersion containing about 20 to 50% by weight of anthraquinone, said dispersion prepared by cyclizing ortho-benzoylbenzoic acid at a temperature of about 150° to 180° C. and at an absolute pressure between about 5 and 40 millibars in the presence of between about 0.5 to 2 parts by weight of sulfuric acid, having a concentration of at least about 95%, per part by weight of ortho-benzoylbenzoic acid to form a reaction mixture containing anthraquinone, bringing the reaction mixture to a pH of at least about 7 by addition thereto at a temperature between about ambient temperature and 100° C. of an aqueous solution of sodium hydroxide or potassium hydroxide containing between about 10% and 40% hydroxide by weight to form a suspension, and then grinding said suspension to form a dispersion thereof containing anthraquinone and the impurities resulting from such reactions.

2. The process of claim 1 wherein said hydroxide is added at a temperature between about 50° C. to 60° C.

3. The process of claim 1 or 2 wherein said hydroxide solution containing from about 20% to 30% hydroxide by weight.

4. The process of claim 1 wherein said dispersion is an aqueous dispersion.

5. The process of claim 1 wherein said dispersion is a powder.

* * * * *